United States Patent
Dunbar

(10) Patent No.: US 8,834,832 B2
(45) Date of Patent: Sep. 16, 2014

(54) PROCESS FOR PRODUCING NANOPARTICLES

(75) Inventor: Timothy D. Dunbar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 284 days.

(21) Appl. No.: 12/746,952

(22) PCT Filed: Dec. 16, 2008

(86) PCT No.: PCT/US2008/086932
§ 371 (c)(1),
(2), (4) Date: Jun. 9, 2010

(87) PCT Pub. No.: WO2009/085731
PCT Pub. Date: Jul. 9, 2009

(65) Prior Publication Data
US 2010/0266485 A1 Oct. 21, 2010

Related U.S. Application Data

(60) Provisional application No. 61/015,990, filed on Dec. 21, 2007, provisional application No. 61/016,048, filed on Dec. 21, 2007.

(51) Int. Cl.
| | | |
|---|---|---|
| *C01G 1/02* | (2006.01) | |
| *C01G 9/02* | (2006.01) | |
| *C01G 23/04* | (2006.01) | |
| *C01G 31/02* | (2006.01) | |
| *C01G 45/02* | (2006.01) | |
| *C01G 37/02* | (2006.01) | |
| *C01F 7/02* | (2006.01) | |
| *C01G 15/00* | (2006.01) | |
| *C01G 19/02* | (2006.01) | |
| *C01G 21/02* | (2006.01) | |
| *C09C 1/04* | (2006.01) | |
| *B82Y 30/00* | (2011.01) | |
| *C09C 3/08* | (2006.01) | |

(52) U.S. Cl.
CPC ............. *C09C 1/043* (2013.01); *C01G 37/02* (2013.01); *C01P 2004/64* (2013.01); *C01G 15/00* (2013.01); *C01G 19/02* (2013.01); *C01G 1/02* (2013.01); *B82Y 30/00* (2013.01); *C01G 9/02* (2013.01); *C01G 31/02* (2013.01); *C01G 45/02* (2013.01); *C09C 3/08* (2013.01); *C01G 23/04* (2013.01); *C01G 21/02* (2013.01); *C01F 7/02* (2013.01); *Y10S 977/773* (2013.01); *Y10S 977/811* (2013.01)
USPC ...... 423/622; 423/608; 423/594.17; 423/605; 423/606; 423/625; 423/624; 423/621; 423/618; 423/619; 977/773; 977/811

(58) Field of Classification Search
CPC ...... C01P 2004/64; C01G 9/02; C01G 23/04; C01G 45/02; C01G 37/02; C01G 15/00; C01G 19/02; C01G 21/02; C01G 1/02; C01F 7/02
USPC ............. 423/592.1, 606, 607, 608–610, 617, 423/618, 619, 622, 624, 625, 632, 633, 423/594.17, 594.19, 69, 62, 22, 53, 58, 138, 423/99, 111, 115, 89, 593.1, 594.1, 594.3, 423/594.5, 595, 598, 599, 600, 601, 594.7, 423/594.8, 594.9, 594.14, 605, 621; 977/773–777, 810, 811
See application file for complete search history.

(56) References Cited

U.S. PATENT DOCUMENTS

| | | |
|---|---|---|
| 3,389,170 A | 6/1968 | Habicht et al. |
| 4,047,965 A | 9/1977 | Karst et al. |
| 4,089,996 A | 5/1978 | Lange et al. |
| 4,159,205 A | 6/1979 | Miyahara et al. |
| 4,277,269 A | 7/1981 | Sweeting |
| 4,588,575 A | 5/1986 | David |
| 4,778,671 A * | 10/1988 | Wusirika .................. 423/592.1 |
| 4,954,462 A | 9/1990 | Wood et al. |
| 5,071,635 A | 12/1991 | Yamanaka et al. |
| 5,635,154 A * | 6/1997 | Arai et al. .................... 423/263 |

(Continued)

FOREIGN PATENT DOCUMENTS

| | | |
|---|---|---|
| EP | 0 317 272 | 5/1989 |
| WO | WO 02/49684 | 6/2002 |

(Continued)

OTHER PUBLICATIONS

Gogotsi, "Nanomaterials Handbook", CRC Press Jan. 26, 2006, p. 23.*

(Continued)

*Primary Examiner* — Stanley Silverman
*Assistant Examiner* — Justin Bova
(74) *Attorney, Agent, or Firm* — Lucy C. Weiss

(57) ABSTRACT

A process comprises (a) combining (1) at least one base and (2) at least one metal carboxylate salt comprising (i) a metal cation selected from metal cations that form amphoteric metal oxides or oxyhydroxides and (ii) a lactate or thiolactate anion, or metal carboxylate salt precursors comprising (i) at least one metal salt comprising the metal cation and a non-interfering anion and (ii) lactic or thiolactic acid, a lactate or thiolactate salt of a non-interfering, non-metal cation, or a mixture thereof; and (b) allowing the base and the metal carboxylate salt or metal carboxylate salt precursors to react.

17 Claims, 1 Drawing Sheet

(56) References Cited

U.S. PATENT DOCUMENTS

| | | | |
|---|---|---|---|
| 6,200,680 B1 * | 3/2001 | Takeda et al. | 428/402 |
| 6,376,590 B2 | 4/2002 | Kolb et al. | |
| 6,387,981 B1 | 5/2002 | Zhang et al. | |
| 6,710,091 B1 | 3/2004 | Womelsdorf et al. | |
| 2002/0004544 A1 | 1/2002 | Kolb et al. | |
| 2003/0175217 A1 | 9/2003 | Kropf et al. | |
| 2004/0023824 A1 | 2/2004 | Zuechner et al. | |
| 2004/0033270 A1 | 2/2004 | Kropf et al. | |
| 2005/0048010 A1 | 3/2005 | Kliss et al. | |
| 2008/0286362 A1 | 11/2008 | Baran et al. | |

FOREIGN PATENT DOCUMENTS

| | | |
|---|---|---|
| WO | WO 2008/079800 | 7/2008 |
| WO | WO 2009/085721 | 7/2009 |
| WO | WO 2009/085731 | 7/2009 |
| WO | WO 2009/110945 | 9/2009 |

OTHER PUBLICATIONS

Meulenkamp, E. A., "Synthesis and Growth of ZnO Nanoparticles," *J. Phys. Chem. B*, 102, 5566-5572 (1998).

Wong, E. M.; Searson, P. C.; Bonevich, J. E. "Growth Kinetics of Nanocrystalline ZnO Particles From Colloidal Suspensions," *J. Phys. Chem. B*, 102, 7770-7775 (1998).

Xiong, H. M.; Liu, D. P.; Chen, J. S.; Xia, Y. Y. "Polyether-Grafted ZnO Nanoparticles With Tunable and Stable Photoluminescence at Room Temperature," *Chem. Mater*. 17, 3062-3064 (2005).

Y. Qi, P. Chen, T. Wang, X. Hu, and S. Zhou, "Fabrication of Self-Assembled PEDOT/PSS-ZnO Nanocables with Diverse Inner Core Sizes Facilitated by Vacuum Conditions," *Macromolecular Rapid Communications* 27, 356-360 (2006).

Z. Hu, P.C. Searson, J.F. Herrera Santos, and G. Oskam, "Influence of the Reactant Concentrations on the Synthesis of ZnO Nanoparticles," *Journal of Colloid and Interface Science* 288, 313-316 (2005).

Silva et al., "Morphology of nanometric size particulate aluminium-doped zinc oxide films," *Colloids and Surfaces*, A: Physicochemical and Engineering Aspects 198-200, 551-558 (2002).

Silva et al., "Aluminium doped zinc oxide films: formation process and optical properties," *Journal of Non-Crystalline Solids* 247, 248-253 (1999).

Tang et al., "Aluminum-doped zinc oxide transparent conductors deposited by the sol-gel process," *Thin Solid Films* 238, 83-87 (1994).

Silva et al., "Aluminium-doped zinc oxide films prepared by an inorganic sol-gel route," *Science Direct, Thin Solid Films* 449, 86-93 (2004).

Yingqun, "Fabrication of PEDOT/PSS-ZnO nanowire by self-assembly method under vacuum condition," *Chinese Science Bulletin* 50 (20), 2288-2290 (2005).

Venkatachari et al., Ceram. Eng. Sci. Proc., Preparation of Mullite-Based Fibers by Sol-Gel Processing, 11[9-10], pp. 1512-1525 (1990).

International Search Report PCT/US2008/086932.

"Carbonyl Compounds I" in unknown book title, author(s), and publisher, Chapter 17, pp. 670-674, 681-687, and 712, http://depa.fquim.unam.mx/amyd/archivero/CarboniloYurkanis_10059.pdf).

* cited by examiner

PROCESS FOR PRODUCING NANOPARTICLES

STATEMENT OF PRIORITY

This application claims the priority of U.S. Provisional Application Nos. 61/015,990 and 61/016,048, both filed on Dec. 21, 2007, the contents of which are hereby incorporated by reference.

FIELD

This invention relates to processes for producing metal oxide or metal oxyhydroxide particles.

BACKGROUND

Metal oxides have numerous uses. In particular, zinc oxide is used for diverse purposes including, for example, use as a white pigment, as a catalyst, as a constituent of antibacterial skin-protection ointment, and as an activator for rubber vulcanization. Sunscreens and wood varnishes contain finely divided zinc oxide as an ultraviolet (UV)-absorbing pigment.

Zinc oxide is useful as a UV-absorbing agent because it does not degrade upon prolonged exposure to UV light. When its particle size is less than about 20 nanometers (nm), however, its bandgap shifts to higher energy as its particle size decreases, due to quantum confinement. To maximize the number of UV wavelengths absorbed by zinc oxide, particles having a bandgap as close as possible to the semiconductor's bulk bandgap are desirable. Since the shift from the bandgap of the bulk material is greater the smaller the particle size, crystalline particle diameters of at least about 5 nm generally can be useful. Such particle diameters provide bandgap values relatively close to those of the bulk material, resulting in a relatively broad range of absorbed wavelengths.

Nanoparticles of zinc oxide can be sufficiently small, however, so as to scatter only negligible amounts of visible light. Thus, UV light absorbing, but visible light transparent, composites (for example, transparent organic-inorganic hybrid materials, plastics, paints and coatings) can be made using zinc oxide nanoparticles as a filler. To maintain optical transparency, particle diameters (and the diameters of any agglomerates present) generally should be less than about one-tenth the wavelength of light (for example, below about 30 nm).

The preparation of zinc oxide by both dry and wet processes is known. The classical dry method of burning zinc generates aggregated particles having a broad size distribution. Particularly finely divided zinc oxide is prepared predominantly by wet chemical methods using precipitation processes. Precipitation in aqueous solution generally gives hydroxide- and/or carbonate-containing materials that require thermal conversion to zinc oxide. The thermal post-treatment can have a negative effect on the finely divided nature of the particles, as the particles are subjected during this treatment to sintering processes that can lead to the formation of micrometer (μm)-sized aggregates. These aggregates can be broken down only incompletely to the primary particles by milling or grinding.

In non-aqueous solutions (or aqueous solutions above the decomposition temperature of zinc hydroxide), zinc oxide can be grown through a simple base precipitation according to the following equation (where X is generally a suitable anion and Y is a suitable cation):

$$ZnX_2 + 2YOH \rightarrow ZnO + 2YX + H_2O$$

Particle growth takes place through an Ostwald ripening process and is diffusion-dependent. As such, particle growth is rather slow at room temperature if 8 nm or larger diameter particles are desired. Elevating the reaction temperature can speed the process to reasonable rates, but this can simultaneously increase the rate of agglomeration.

Various common zinc salts (for example, zinc acetate) have been used as the starting salt in such non-aqueous precipitation processes. However, such starting salts have generally required the use of dilute solutions to avoid relatively high rates of agglomeration, and zinc oxide grown from such salts has tended to form agglomerates that are unsuitable for applications requiring transparency.

Other processes for the preparation of nanosize zinc oxide particles utilize expensive starting materials (for example, zinc alkoxides), require the use of emulsifiers, are complex, provide agglomerates, provide slow particle growth, provide insufficient control over particle size, and/or cannot provide often preferred particle sizes (for example, average primary particle diameters of about 5 to about 30 nm).

SUMMARY

Thus, we recognize that there is a need for processes for producing metal oxide or metal oxyhydroxide nanoparticles (particularly, zinc oxide nanoparticles) that can minimize or even eliminate particle agglomeration, while allowing for particle growth to desired primary particle sizes. Preferred processes will be simple, cost-effective, and/or enable control of final particle size.

Briefly, in one aspect, this invention provides such a process, which comprises (a) combining (preferably, in at least one solvent) (1) at least one base and (2) at least one metal carboxylate salt comprising (i) a metal cation selected from metal cations that form amphoteric metal oxides or oxyhydroxides (most preferably, zinc) and (ii) a lactate or thiolactate anion (preferably, a lactate anion), or, alternatively, metal carboxylate salt precursors comprising (i) at least one metal salt comprising the metal cation and a non-interfering anion (that is, an anion that is not reactive with the base) and (ii) lactic or thiolactic acid (preferably, lactic), a lactate or thiolactate salt (preferably, lactate) of a non-interfering, non-metal cation (for example, tetraalkylammonium; preferably, tetramethylammonium), or a mixture thereof; and (b) allowing the base and the metal carboxylate salt or metal carboxylate salt precursors to react (for example, to form a metal oxide or metal oxyhydroxide).

It has been discovered that use of the above-described metal carboxylate salts or metal carboxylate salt precursors in a basic precipitation process can enable the preparation of substantially non-agglomerated metal oxide or metal oxyhydroxide nanoparticles. In addition, the salts or their precursors can enable nanoparticles to be grown to preferred larger average primary particle sizes (for example, average primary particle diameters above 4-5 nm). Preferred embodiments of the process can enable control of average primary particle size by varying, for example, the reaction temperature and/or time.

Thus, the process of the invention can be especially advantageous for producing zinc oxide nanoparticles. The process can be used to provide, for example, zinc oxide nanoparticles having average primary particle diameters in the range of about 5 nm to about 10 nm or more. Such nanoparticles can be well-suited for use in making UV light absorbing, visible light transparent composites, with the particle size control that is provided by the process further enabling a tuning of absorption characteristics.

The process of the invention, in addition, is relatively simple and utilizes metal carboxylate salts or metal carboxylate salt precursors that are relatively inexpensive starting compounds. Thus, in at least preferred embodiments, the process can meet the above-mentioned need in the art for simple, cost-effective processes for producing metal oxide or metal oxyhydroxide nanoparticles (particularly, zinc oxide nanoparticles) that can minimize particle agglomeration, while allowing for particle growth to desired primary particle sizes.

BRIEF DESCRIPTION OF DRAWING

These and other features, aspects, and advantages of the present invention will become better understood with regard to the following description, appended claims, and accompanying drawing, wherein:

DETAILED DESCRIPTION

Definitions

Figure 1:
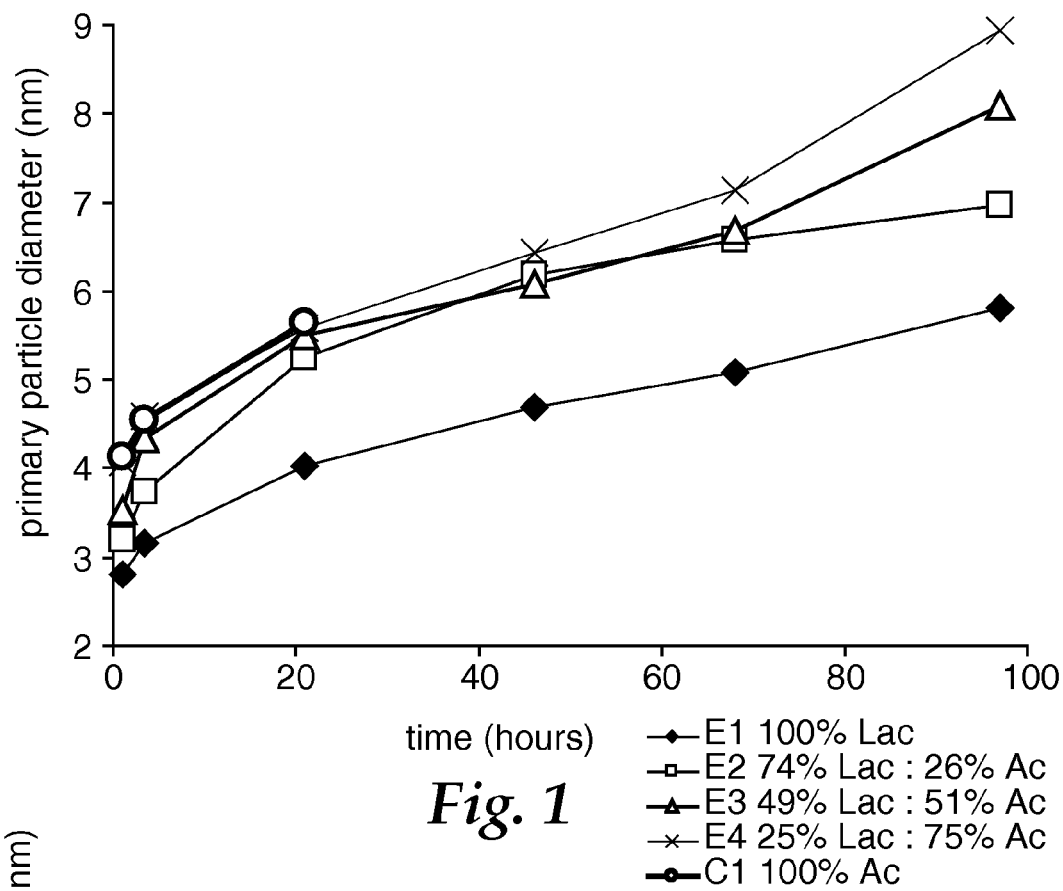
FIG. 1 is a plot of average primary particle diameter versus time for the process embodiments described in Comparative Example 1 (using only zinc acetate, $Zn(Ac)_2$) and Examples 1, 2, 3, and 4 (using varying ratios of $Zn(Ac)_2$ to zinc lactate, $Zn(Lac)_2$).

As used in this patent application:

"agglomeration" means an association of primary particles, which can range from relatively weak (based upon, for example, charge or polarity) to relatively strong (based upon, for example, chemical bonding);

"amphoteric" (in reference to a metal oxide or metal oxyhydroxide) means able to function as both a Bronsted/Lowry acid and base;

"nanoparticles" means particles having a diameter of less than about 100 nm;

"primary particle size or diameter" means the size or diameter of a non-associated single crystal particle; and "sol" means a dispersion or suspension of colloidal particles in a liquid phase.

Bases

Bases that can be suitable for use in the process of the invention include hydroxyl group-containing basic compounds and mixtures thereof. Useful compounds include sodium hydroxide, potassium hydroxide, ammonium hydroxide, tetramethylammonium hydroxide, and the like, and mixtures thereof. Preferred bases include sodium hydroxide (for example, due to its relatively low cost), tetramethylammonium hydroxide (for example, due to its solubility in a wide variety of organic solvents), and mixtures thereof. Tetramethylammonium hydroxide is more preferred.

The base can be used in solid form (for example, as NaOH or KOH pellets) or in the form of a solution in a polar organic solvent (for example, an alkanol such as methanol). A wide range of concentrations can be useful (for example, tetramethylammonium hydroxide can be used in a commercially available concentration of 25 weight percent in methanol). In a preferred embodiment of the process of the invention, the base can be added in solution form to a solution of metal carboxylate salt or metal carboxylate salt precursors. Solvents useful for dissolving the base include acetone, diethyl ether, alkanols (for example, methanol, ethanol, and isopropanol), dimethylsulfoxide (DMSO), dimethylformamide (DMF), tetrahydrofuran (THF), ethyl acetate, and the like, and mixtures thereof, with alkanols being preferred and methanol more preferred.

Salts

Metal carboxylate salts suitable for use in the process of the invention include those that comprise (i) a metal cation selected from metal cations that form amphoteric metal oxides or oxyhydroxides and (ii) a lactate or thiolactate anion. Suitable metals include Be, Ti, V, Mn, Cr, Fe, Co, Ni, Al, Zn, Ga, In, Ge, Sn, Pb, As, Sb, Bi, Te, Po, and the like, and mixtures thereof. Preferred cations of such metals include $Be^{+2}$, $Ti^{+4}$, $V^{+4}$, $V^{+5}$, $Mn^{+4}$, $Cr^{+3}$, $Cr^{+4}$, $Fe^{+3}$ $Fe^{+4}$ $Co^{+3}/Co^{+2}$ (mixed oxidation state compound), $Ni^{+3}$, $Ni^{+4}$, $Al^{+3}$, $Zn^{+2}$, $Ga^{+3}$, $In^{+3}$, $Ge^{+2}$, $Sn^{+2}$, $Sn^{+4}$, $Pb^{+2}$, $As^{+3}$, $Sb^{+3}$, $Bi^{+3}$, $Te^{+4}$, $Po^{+4}$, and the like, and mixtures thereof.

Preferred metals include Ti, V, Mn, Cr, Al, Zn, Ga, In, Sn, Pb, and mixtures thereof. More preferred are Ti, Al, Zn, Ga, In, and mixtures thereof, with Zn being most preferred. If desired, the salts can comprise other metal cations (non-amphoteric) (for example, at levels up to about 10 mole percent, based upon the total number of moles of metal cation), but preferably all metals in the salt are selected from those that form amphoteric metal oxides or oxyhydroxides.

A class of useful metal carboxylate salts can be represented by the following general formula $$[CH_3CH(Y)COO^-]_m[X^-]_n M^{+(m+n)} \qquad (I)$$

wherein each Y is independently —OH or —SH; X is a non-interfering anion (that is, an anion that is not reactive with base); m and n are integers having values such that the sum m+n is equal to the charge of the metal cation, M; and at least about 90 mole percent (preferably, at least about 95 mole percent; more preferably, about 100 mole percent) of M (based upon the total number of moles of metal cation) is selected from Be, Ti, V, Mn, Cr, Fe, Co, Ni, Al, Zn, Ga, In, Ge, Sn, Pb, As, Sb, Bi, Te, Po, and mixtures thereof.

Preferably, Y is —OH; X is an anion selected from halide, nitrate, acetate, carbonate, formate, propionate, sulfate, bromate, perchlorate, tribromoacetate, trichloroacetate, trifluoroacetate, $R'(OR)_xZ(OR)_w(CH_2)_yCOO^-$ (wherein R' is a linear or branched alkyl group having from 1 to about 4 carbon atoms, each R is independently a linear or branched alkylene moiety having from 1 to about 4 carbon atoms, x is an integer of 0 to 4, Z is a divalent organic linking moiety (for example, a moiety non-directionally selected from the group consisting of a covalent bond, —S—, —C(O)O—, —C=C—, and —C(O)NH—, and combinations thereof), w is an integer of 0 to 4 with the proviso that the sum of x+w is an integer of 1 to 4, and y is an integer of 0 to about 3), and chlorate ions, and mixtures thereof (more preferably, selected from chloride, acetate, and mixtures thereof; most preferably, acetate); and/or M is selected from Ti, V, Mn, Cr, Al, Zn, Ga, In, Sn, Pb, and mixtures thereof (more preferably, Ti, Al, Zn, Ga, In, and mixtures thereof; most preferably, zinc).

Representative examples of useful metal carboxylate salts include metal lactates, metal thiolactates, and mixtures thereof, where the hierarchy of metal preferences is as set forth above. More preferred metal carboxylate salts include zinc lactate, zinc thiolactate, and mixtures thereof. Zinc lactate (which can be represented as $Zn(Lac)_2$) is most preferred.

Such metal carboxylate salts can be prepared from the corresponding metal salts having anions that can be displaced with lactic or thiolactic acid. Useful starting metal salts include metal oxynitrates, metal oxychlorides, metal carbonates, metal acetates, metal formates, metal propionates, metal nitrates, metal chlorides, metal oxides, metal hydroxides, metal oxyhydroxides, and the like, and combinations thereof. Many of such salts are commercially available. Metal lactates and metal thiolactates can be obtained from the reaction of such starting metal salts with lactic or thiolactic acid, commercially available from Aldrich Chemical Company, St. Louis, Mo.

The lactic or thiolactic acid can be, for example, added to an aqueous solution of a starting metal salt, and then the resulting mixture can be dried, for example, overnight in an oven at about 120° C. Alternatively, a base (for example, sodium hydroxide) can be added to an aqueous solution of starting metal salt to form a precipitate (for example, a metal hydroxide), which can be collected (for example, by filtration), washed (for example, in relatively cold water), and dispersed in water prior to lactic or thiolactic acid addition. The resulting mixture can be reacted by heating, for example, to about 70° C. with overnight stirring. The resulting metal carboxylate salt can be isolated (for example, by filtration followed by rotary evaporation of the resulting filtrate) and dried (for example, in a vacuum oven). Other orders and manners of combination of the starting metal salt and the lactic or thiolactic acid can be utilized. Stoichiometric amounts of the starting metal salt and the acid generally can be used, although a stoichiometric excess of either reactant can be useful.

The above-described metal carboxylate salt(s) can be used in the process of the invention in combination with one or more other salts (for example, salts such as zinc acetate) having only non-interfering anions (as defined above in reference to Formula I), if desired. Preferably, at least about 50 mole percent of such a combination, however, will be the above-described metal carboxylate salt(s). If desired, the other salts having non-interfering anions can comprise other metal cations (for example, at levels up to about 10 mole percent, based upon the total number of moles of metal cation), but preferably all metals in the other salts are selected from those that form amphoteric metal oxides or oxyhydroxides.

Solvents

Solvents that can be suitable for use in carrying out the process of the invention include those in which the metal carboxylate salts or salt precursors and bases can be substantially soluble. Such solvents include polar organic solvents (for example, dimethylsulfoxide (DMSO), dimethylformamide (DMF), acetonitrile, alkanols (for example, methanol, ethanol, isopropanol, 1-methoxy-2-propanol, and the like, and mixtures thereof), N-methylpyrrolidinone (NMP), water (for example, at temperatures above the zinc hydroxide decomposition temperature when using zinc carboxylate salts), and the like, and mixtures thereof.

Preferred solvents can include DMSO, DMF, acetonitrile, NMP, and mixtures thereof (with DMSO being more preferred), due to the relatively high solubility of metal lactates and thiolactates in such solvents. Preferred solvents alternatively can include alkanols (preferably, 1-methoxy-2-propanol), however, due to their ease of removal during purification. Most preferably, the solvent will be capable of dissolving the reactants and products of the process, while keeping the desired metal oxide nanoparticles well-dispersed.

Process

The process of the invention can be carried out by combining at least one base and at least one metal carboxylate salt (preferably, in at least one solvent). Alternatively, but less preferably, the process can be carried out by substituting metal carboxylate salt precursors for the metal carboxylate salt. Such precursors can comprise (i) at least one metal salt comprising a metal cation (selected from metal cations that form amphoteric metal oxides or oxyhydroxides, as described above) and a non-interfering anion (that is, an anion that is not reactive with the base, as described above) and (ii) lactic or thiolactic acid, a lactate or thiolactate salt of a non-interfering, non-metal cation (for example, tetraalkylammonium; preferably, tetramethylammonium), or a mixture of any two or more thereof (preferably, lactic acid, lactate salt(s), or a mixture thereof more preferably, lactate salt(s)). A class of useful metal salts can be represented by the following general formula

$$M^{+n}[X^-]_n \qquad (II)$$

wherein M, X, and n are as defined above for Formula I. In this alternative process, an excess amount of base relative to the amount needed to neutralize all of the lactic or thiolactic acid can be utilized to allow reaction of base with the metal present. This alternative process generates one mole of water for each mole of acid neutralized. Water in relatively small amounts can speed the kinetics of growth of ZnO nanoparticles, but the presence of water in relatively larger amounts can cause agglomeration.

Generally, any order and manner of combination of reactants can be utilized, although it can sometimes be preferable to dissolve each reactant separately in solvent prior to combination. Preferably, a substoichiometric amount of base relative to the amount of metal carboxylate salt or salt precursors (especially when the salt is a zinc carboxylate) can be utilized (for example, to ensure that the resulting metal oxide stays well-dispersed).

Mechanical agitation or stirring can be used, if desired, to facilitate mixing. Optionally, heating can be used to facilitate dissolution, reaction, and/or primary particle size growth. The reactants can be combined in a pressure vessel, if desired (for example, this can be useful for reactions carried out at temperatures above the boiling point of a selected solvent).

To influence, for example, the morphology, magnetic properties, conductivity, light absorption or emission characteristics, and/or the crystallinity of the resulting nanoparticles, various compounds (foreign ions) can be added before, during, or after nanoparticle precipitation. Preferred additive compounds include 2nd-4th main group and transition metal compounds (more preferably, cobalt, gallium, indium, manganese, magnesium, silicon, and aluminum compounds, and mixtures thereof; most preferably, aluminum, gallium, indium, and silicon compounds, and mixtures thereof). Such additive compounds preferably can be added to the reactant combination in dissolved form and/or preferably can be used in an amount from about 0.01 to about 10 mole percent, based on the total number of moles of metal (present, for example, in the form of metal lactate or thiolactate).

The resulting nanoparticles can be isolated (for example, from a resulting sol) and/or purified by using standard techniques such as decantation (for example, following centrifugation or settling optionally induced by cosolvent addition), filtration, rotary evaporation for solvent removal, dialysis, diafiltration, and the like, and combinations thereof. The characteristics of the resulting product can be evaluated by ultraviolet-visible spectroscopy (absorption characteristics), X-ray diffraction (crystalline particle size, crystalline phase, and particle size distribution), transmission electron microscopy (particle sizes, crystalline phase, and particle size distributions), and dynamic light scattering (degree of agglomeration).

The resulting nanoparticles can be used, for example, in organic-inorganic hybrid materials (for example, for the UV protection of polymers, paints, coatings, and the like). Preferred embodiments of the process of the invention can provide nanoparticles useful in making UV light absorbing, visible light transparent composites.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Sigma-Aldrich Chemical Company, St. Louis, Mo., unless otherwise noted.

Primary Particle Size Determination

The ultraviolet (UV)-visible (Vis) spectrometer used to monitor primary particle sizes was a PerkinElmer™ Lambda 35 instrument (available from PerkinElmer Life and Analytical Sciences, Wellesley, Mass.) with 1 cm path length UV-grade quartz sample cells or cuvettes. A small aliquot of experimental sample was withdrawn from its vial and diluted with organic solvent (for example, 200 proof absolute ethanol, USP grade, Aaper Alcohol and Chemical Co., Shelbyville, Ky.). The diluted sample was then shaken well to mix, and approximately 2.5 mL was transferred to a cuvette for UV-visible spectroscopy. The UV-Vis spectrometer was scanned from 500 to 280 nm, at a rate of 1920 nm per minute, using a slit width set for 1 nm and a data collection interval of 1 nm. The spectrometer was set to change from the visible light lamp to the UV light lamp at 326 nm.

The location of the absorption edge of the sample was determined by differentiating the absorbance versus wavelength curve with respect to wavelength, using the Savitzsky-Golay procedure supplied with the spectrometer software, where the width parameter was set to 9. In differentiating the absorbance versus wavelength curve, the spectrometer software calculated the negative of the differentiated absorbance versus wavelength curve, so that a curve with a positive peak was the result. The wavelength of the maximum of this peak was taken to be the absorption edge position, $\lambda'_{max}$. The following equation, described by E. A. Meulenkamp in Journal of Physical Chemistry, B, 102, 5556-5572 (1998), was used to determine the particle diameter (d, in nm) from the absorption edge position ($\lambda'_{max}$, also in nm).

$$d=\{0.017+[(334.56/\lambda'_{max})-0.8904]^{1/2}\}/[(375.64/\lambda'_{max})-1]$$

Because light scattering leads to an incorrect measurement of absorbance and therefore an incorrect determination of primary particle size, primary particle sizes were not calculated when samples scattered to an appreciable amount (for example, due to significant agglomeration). This appreciable amount was defined as the absorbance at 400 nm divided by the absorbance at the top of the absorption edge. When this number was greater than 0.2, no primary particle sizes were calculated.

Zinc Oxide Concentration Determination

The concentration of zinc oxide in selected dispersions was determined by measuring the height of the UV-visible absorption edge of the dispersion and multiplying by a reported zinc oxide nanoparticle extinction coefficient times the dilution factor of the dispersion. (An extinction coefficient of 0.135 mg mL$^{-1}$ A$^{-1}$ cm$^{-1}$ has been reported for zinc oxide nanoparticles approximately 4 nm in diameter by Hu et al. in Journal of Colloid and Interface Science, 288, 313-316 (2005), and this number was used in all calculations). The height of the absorption edge was often not clear, since the feature was an edge and not a distinct peak. To reproducibly calculate the absorption edge height and to compensate for absorption edges with varying widths, the following procedure was used.

The $\lambda'_{max}$ of the peak occurring in the $\lambda'$ (differentiated absorbance) curve was determined as described above. The full-width-at-half-maximum (FWHM) of the peak was then determined as follows. A left minimum position of the peak was taken as the differentiated absorbance value of the minimum of the $\lambda'$ curve in the range of between 15 nm and 45 nm lower in wavelength than $\lambda'_{max}$. A right minimum position of the peak was taken as the differentiated absorbance value on the $\lambda'$ curve that was 30 nm greater in wavelength than $\lambda'_{max}$. Left and right halfway points of the peak in the differentiated absorbance curve (points that were halfway from the base of the peak to the maximum of the peak) were determined by averaging the maximum and the respective minimum points. The FWHM was then determined by subtracting the wavelength value of the left halfway point (shorter wavelength) from the wavelength value of the right halfway point (longer wavelength).

After the FWHM was determined, the absorbance value of the absorption edge of the dispersion was calculated. In order to account for baseline offsets in the absorbance curve, the absorption edge was baselined by subtracting the absorbance value of a point at the bottom of the absorption edge from the absorbance value of a point at the top of the absorption edge. The absorbance value of the point at the top of the absorption edge was the absorbance value at a wavelength corresponding to $\lambda'_{max}$ minus 1.3 times the FWHM. The absorbance value of the point at the bottom of the absorption edge was the absorbance value at a wavelength corresponding to $\lambda'_{max}$ plus 1.3 times the FWHM. The final, reported absorbance value for the absorption edge was the result of subtracting the bottom (lower) absorbance value from the top (higher) absorbance value.

Decree of Agglomeration

Dynamic light scattering measurements were made using a Malvern NANOSIZER Nano-ZS, Model Number ZEN-3600, particle size analyzer (available from Malvern Instruments, Malvern, U.K.) and were used to monitor the agglomeration of particles over time. A small (1 g) aliquot was taken from a sample vial in an oil bath and diluted with 1 g dimethylsulfoxide (DMSO). The diluted sample was mixed well and then transferred to a glass cuvette. Light scattering data was recorded with the sample temperature set at 25° C. In transforming the resulting autocorrelation function into particle size, the viscosity (1.98×10$^{-3}$ Pa·s; 1.98 cP) and refractive index (1.479) of dimethylsulfoxide were used. The reported agglomerated particle diameter was based upon an intensity weighted distribution.

Preparation of Zinc Diglycolate

Zinc diglycolate was prepared by a modified version of the procedure described by H. M. Xiong et al. in Chemistry of Materials 17, 3062-3064 (2005). To a solution of zinc chloride (13.63 g, 0.1 mole, Alfa Aesar, Ward Hill, Mass.) in water (20 g) was added sodium hydroxide (207 mL of 1.0 N solution in water, Mallincrodt Baker, Phillipsburg, N.J.). A white precipitate (zinc hydroxide) formed immediately. The resulting mixture was stirred vigorously for one hour, chilled, and filtered. The resulting solids were washed three times with 200 mL cold water. The washed solids (white in color) were then dried for one hour in an oven at 70° C. The dried solids were then slurried in 50 g deionized water and heated to 70° C. To this slurry was added diglycolic acid (13.41 g, 0.1 mole, Alfa Aesar, Ward Hill, Mass.) mixed in 20 g of deionized water. The resulting zinc hydroxide and diglycolic acid slurry was allowed to react overnight at 70° C. with stirring. A major portion of the water was removed from the slurry by rotary evaporation. The remaining water was removed by drying in a vacuum oven at 100° C. overnight.

Preparation of Zinc 3,6-Dioxadioctanedioate

Zinc 3,6-dioxadioctanedioate was prepared by essentially the procedure described above for zinc diglycolate, with the exception that 3,6-dioxadioctanedioic acid (17.81 g, 0.1 mole) was substituted for the diglycolic acid.

Preparation of Zinc 3,6,9-Trioxaundecanedioate

Zinc 3,6,9-trioxaundecanedioate was prepared by essentially the procedure described above for zinc diglycolate, with the exception that 3,6,9-trioxaundecanedioic acid (23.86 g, 0.107 mole) was substituted for the diglycolic acid and was added directly to the water/zinc hydroxide slurry.

Preparation of Zinc Adipate

Zinc adipate was prepared by essentially the procedure described above for zinc diglycolate, with the exception that adipic acid (14.65 g, 0.1 mole, Fisher Scientific, Hampton, N.H.) was substituted for the diglycolic acid.

Examples 1-4 and Comparative Example 1

Zinc lactate (Pfaltz & Bauer, Waterbury, Conn.) was dried in a vacuum oven overnight at 100° C. Thermal gravimetric analysis (TGA) of the zinc lactate was conducted before and after drying. The temperature in the thermal gravimetric analyzer was raised at a rate of 20° C. per minute up to a temperature of 120° C., and this temperature was held for 20 minutes. Before drying in the vacuum oven, the zinc lactate contained 15.7 weight percent water. After drying, the zinc lactate contained 2.4 weight percent water.

Zinc oxide was synthesized using various ratios of zinc lactate ($Zn(Lac)_2$) to zinc acetate ($Zn(Ac)_2$). A 0.52 mmole per gram stock solution of $Zn(Ac)_2$ was prepared by dissolving 2.75 g dry zinc acetate (Alfa Aesar, Ward Hill, Mass., 183.5 g/mole) in 26.35 g dimethylsulfoxide (DMSO, EMD Chemicals, Gibbstown, N.J., OMNISOLV grade). Various amounts of $Zn(Lac)_2$ and DMSO were added to portions of the stock solution to prepare a series of samples as shown in Table 1 below.

TABLE 1

| Example Number | Amount of $Zn(Lac)_2$ (g) | Amount $Zn(Ac)_2$ Stock Solution (g) | Mole Percent $Zn(Lac)_2$ | Mole Percent $Zn(Ac)_2$ |
| --- | --- | --- | --- | --- |
| 1 | 0.91 | 0 | 100 | 0 |
| 2 | 0.66 | 1.85 | 74 | 26 |
| 3 | 0.45 | 3.7 | 49 | 51 |
| 4 | 0.23 | 5.55 | 25 | 75 |
| C-1 | 0 | 7.4 | 0 | 100 |

Figure 2:
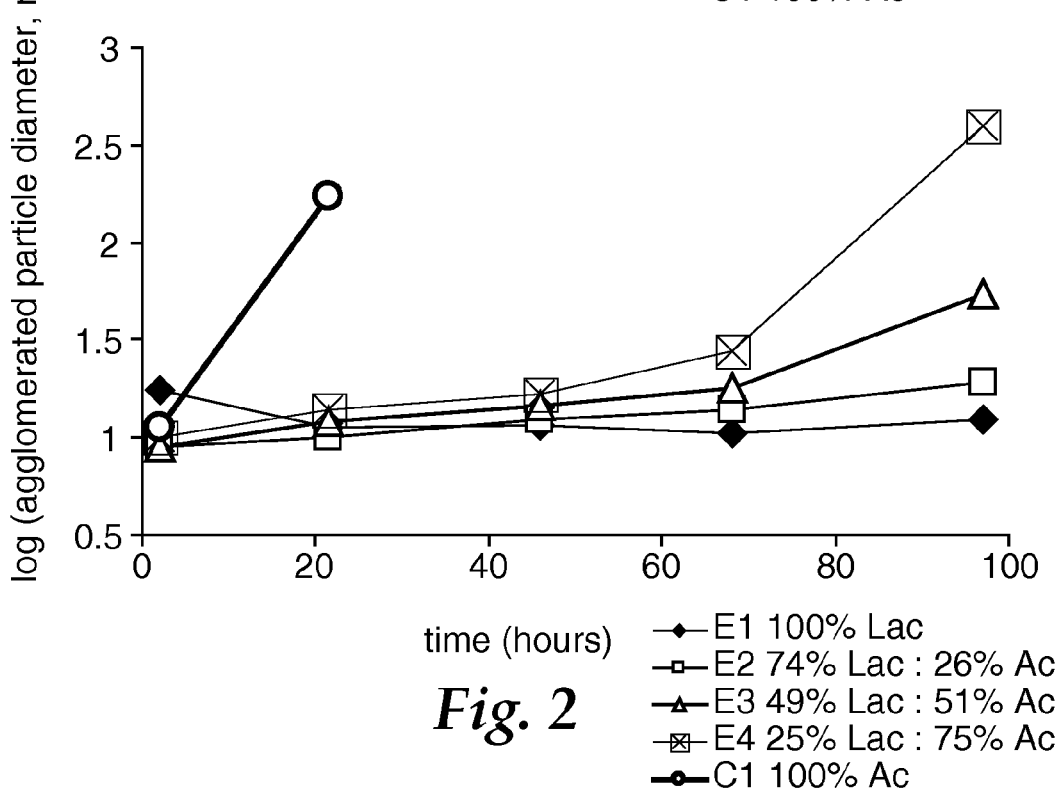
FIG. 2 is a plot of the log of average agglomerated particle diameter versus time for the process embodiments described in Comparative Example 1 (using only zinc acetate, $Zn(Ac)_2$) and Examples 1, 2, 3, and 4 (using varying ratios of $Zn(Ac)_2$ to zinc lactate, $Zn(Lac)_2$).

Each sample was placed in a 40 mL vial, to each of which was added 20.3 g DMSO and a magnetic stir bar. Each vial was then placed in an oil bath set to 90° C. To each vial was then added 2.3 g of tetramethylammonium hydroxide (25 percent in methanol, Alfa Aesar, Ward Hill, Mass.). Each of the five samples was expected to contain about 1 percent by weight ZnO nanoparticles. The samples were analyzed by UV-visible spectroscopy (using a 50 times dilution effected by diluting a 0.5 g aliquot with 24.5 g 200 proof ethanol) and dynamic light scattering at various time intervals. The results are displayed graphically in FIGS. 1 and 2.

Example 5

Zinc lactate (Pfaltz & Bauer, Waterbury, Conn.) was vacuum dried at 100° C. overnight essentially as described above. TGA was carried out essentially as described above and indicated that the zinc lactate contained 4.6 percent by weight water after drying.

DMSO (200 g) was placed in a 1 liter, 3 neck round-bottomed flask. With mechanical stirring, zinc acetate (28.44 g, 0.155 mole, Alfa Aesar, Ward Hill, Mass.) and the vacuum-dried zinc lactate (37.74 g, 0.155 mole) were added as powders to the flask via a powder addition funnel. DMSO (41.9 g) was used to wash residual zinc acetate or zinc lactate remaining on the powder addition funnel into the round-bottomed flask. The flask was placed in a silicone oil bath, the temperature of which was set to 90° C. After the powders were dissolved, 25 percent tetramethylammonium hydroxide in methanol (192.1 g, 0.527 mole, Alfa Aesar, Ward Hill, Mass.) was added to the flask in a steady stream over 15 minutes via a separatory funnel.

The size of the resulting zinc oxide nanoparticles was monitored using UV-visible spectroscopy (essentially as described above) by taking 0.1 mL aliquots of the resulting mixture and diluting them with 23.82 g ethanol. Size measurements were performed hourly until a size of 6.1 nm was reached after three hours of reaction time. The round-bottomed flask was then removed from the oil bath.

To the resulting cooled mixture was added 66 g of 3-(ethylenediamino)propyl-functionalized silica gel, and the resulting mixture was stirred overnight. The resulting slurry was filtered through a bed of Celite™ 521 diatomaceous earth filter agent supported on an ASTM C glass frit funnel filter. The bed of Celite™ 521 diatomaceous earth filter agent and silica gel was rinsed with four portions of 200 proof ethanol, totaling 750 mL. The ethanol and DMSO were stripped via rotary evaporation, first using a water aspirator to provide a vacuum for stripping the ethanol, then using a mechanical pump to provide a vacuum for stripping the DMSO. The resulting solids were re-dispersed in 200 g ethanol to provide a slightly hazy dispersion. This dispersion was filtered through a 1 micron glass fiber membrane syringe filter (Acrodisc™, Pall Life Sciences, East Hills, N.Y.).

Gas chromatography (GC) was used to analyze the resulting ZnO dispersion and showed that there was still 7 weight percent DMSO present, so the ethanol and DMSO were stripped again via rotary evaporator as above. The resulting solids were re-dispersed in 200 g ethanol. GC then showed 3.7 weight percent DMSO present.

The ZnO dispersion in ethanol was further purified through tangential flow filtration (TFF) using a KROSFLO Research II TFF System (Spectrum Labs, Rancho Dominguez, Calif.). The dispersion was diluted from 355 mL to 1600 mL with ethanol. The dispersion was then concentrated to 200 mL on the TFF system using a hollow fiber filter module (Spectrum Labs, Rancho Dominguez, Calif., P/N M11S-260-01N, 615 $cm^2$ filter area, 10 kilodalton cutoff). The flow rate of the peristaltic pump of the TFF system had been set to give a shear value of 9900 $sec^{-1}$. Using the same module, the dispersion was washed with 1000 mL (five volumes) of 200 proof ethanol using the TFF system in diafiltration mode (ethanol lost through the membrane was replaced with fresh ethanol).

UV-visible spectroscopy was used to measure the particle size and determined to be 6.0 nm. The height of the absorption edge in the resulting spectrum was measured as described above, and a zinc oxide concentration of 59 mg mL$^{-1}$ was calculated. With a final dispersion volume of 288 mL, this yielded 17 g of zinc oxide nanoparticles (not including weight of ligand).

Comparative Example 2

Zinc diglycolate (0.73 g, 0.0037 mole) was mixed with 28.04 g of DMSO. The resulting mixture was stirred for 2.5 hours at 70° C. After this time, the mixture was hazy. Tetramethylammonium hydroxide (25 percent in methanol, 2.28 g, 0.0063 mole, Alfa Aesar, Ward Hill, Mass.) was added to the hazy mixture. The mixture quickly became cloudy and white in color.

Comparative Example 3

Zinc 3,6-dioxadioctanedioate (0.90 g, 0.0037 mole) was mixed with 26.86 g DMSO. After stirring for 2.5 hours at 70° C., the mixture was cloudy and white in color. After addition of tetramethylammonium hydroxide (25 percent in methanol, 2.28 g, 0.0063 mole, Alfa Aesar, Ward Hill, Mass.), the mixture remained cloudy and white.

Comparative Example 4

Zinc 3,6,9-trioxaundecanedioate (1.06 g, 0.0037 mole) was mixed with 26.70 g DMSO. After stirring for 2.5 hours at 70° C., a clear solution resulted. After addition of tetramethylammonium hydroxide (25 percent in methanol, 2.28 g, 0.0063 mole, Alfa Aesar, Ward Hill, Mass.), the solution quickly became cloudy and white in color.

Comparative Example 5

Zinc adipate (0.77 g, 0.0037 mole) was mixed with 26.95 g DMSO. After stirring for 2.5 hours at 70° C., the mixture was cloudy and white in color. After addition of tetramethylammonium hydroxide (25 percent in methanol, 2.28 g, 0.0063 mole, Alfa Aesar, Ward Hill, Mass.), the mixture remained cloudy and white.

Analysis of Comparative Examples 2-5

UV-visible spectroscopic analysis was carried out for Comparative Examples 2-5 after 1 and 3.5 hours of heating at 70° C. by taking a small aliquot of each and diluting the aliquot 75 times with 200 proof ethanol. In each case, at each temperature, an absorption edge due to zinc oxide nanoparticles was visible in the spectrum, but there was also significant scattering of visible light.

After 3.5 hours of heating at 70° C., the cloudy, white zinc oxide in DMSO dispersions were each centrifuged (3000 g, 20 minutes), separating each dispersion into a clear, liquid upper layer, and a white, solid lower layer. The liquid layer was decanted, and UV-visible spectroscopy performed on the undiluted liquid. In each case, no zinc oxide was detected above a detection limit of 0.0014 mg mL$^{-1}$. This indicated that there was essentially no unagglomerated zinc oxide in the samples.

Comparative Example 6

Zinc gluconate (Alfa Aesar, Ward Hill, Mass.) was dried in a vacuum oven overnight at 100° C. The dried zinc gluconate (5.63 g, 0.0123 mole) was dissolved in 86.72 g DMSO with heating and magnetic stirring. The resulting solution was allowed to cool to room temperature. Tetramethylammonium hydroxide (25 percent in methanol, 7.65 g, 0.0209 mole, Alfa Aesar, Ward Hill, Mass.) was added to the cooled solution dropwise over five minutes with stirring. Five minutes after base addition had ended, the resulting reaction solution was clear and faintly yellow.

For UV-visible spectroscopy, 0.1 mL of the reaction solution was diluted with 7.4 mL 200 proof ethanol. The UV-visible spectrum of the diluted solution had no absorption edge, indicating that the sample did not contain zinc oxide.

Ninety minutes after base addition had ended, the reaction solution was a yellowish orange color. Another sample of the solution was taken, diluted 75 times with ethanol, and examined using UV-visible spectroscopy. Again, no zinc oxide was detected.

The reaction solution was allowed to stand overnight at room temperature. The next day, the solution was bright orange in color and opaque. A small aliquot (0.1 mL) of the solution was diluted 75 times with DMSO. Again, UV-visible spectroscopy indicated that no zinc oxide had formed.

Comparative Example 7

About two hours after base addition had ended for the reaction solution of Comparative Example 6, 25 g of the solution was withdrawn and placed in another vial. Tetramethylammonium hydroxide (25 percent in methanol, 2.99 g, 0.0082 mole, Alfa Aesar, Ward Hill, Mass.) was added to the withdrawn portion with stirring. The orange color of the portion faded to yellow, became cloudy, and then became clear.

Shortly after this addition of base, a sample (0.1 mL) of the portion was diluted 75 times with ethanol and was examined by UV-visible spectroscopy. No zinc oxide absorption edge was detected.

The portion of reaction solution was allowed to stand overnight at room temperature. The next day, the solution was still yellow and clear. A small aliquot (0.1 mL) of the solution was diluted 75 times with DMSO. Again, UV-visible spectroscopy indicated that no zinc oxide had formed.

Example 6 and Comparative Example 8

Example 6 was carried out by weighing the following into a vial: zinc chloride (0.50 g, 0.0037 mole, Alfa Aesar, Ward Hill, Mass.), 85 percent by weight DL-lactic acid in water (0.78 g, 0.0074 mole, Alfa Aesar, Ward Hill, Mass.), methanol (2.69 g, EMD Chemicals, Gibbstown, N.J., OMNISOLV grade), and DMSO (21.06 g, EMD Chemicals, Gibbstown, N.J., OMNISOLV grade). A stir bar was added, and the vial was placed into a silicone oil bath held at 90° C. The resulting mixture was stirred until a clear solution formed. Tetramethylammonium hydroxide (25 percent by weight in methanol, 4.97 g, 0.0014 mole, Alfa Aesar, Ward Hill, Mass.) was added to the solution dropwise. The solution clouded and then became clear. The solution was heated at 90° C. for five hours, at which time UV-visible spectroscopic and dynamic light scattering analyses were performed. A dilution for UV-visible spectroscopy was prepared by removing 0.1 mL of the solution and adding it to 5.88 g absolute ethanol (7.4 ml, USP grade, Aaper Alcohol and Chemical Co., Shelbyville, Ky.). UV-visible spectroscopy and dynamic light scattering measurements were carried out as described above. The results are shown in Table 2 below.

Comparative Example 8 was carried out in the same manner as Example 6, with the following two exceptions: the 85 percent DL-lactic acid in water was replaced with 85 percent by weight acetic acid in water, which was prepared by combining glacial acetic acid (0.44 g, 0.0074 mole, Mallinkrodt Baker, Phillipsburg, N.J.) and distilled water (0.12 g); and the DMSO amount was increased from 21.06 g to 21.28 g. As in Example 6, the vial was heated to 90° C. and the mixture stirred until a solution formed. Tetramethylammonium hydroxide was then added as in Example 6. After addition of the base, the solution clouded and then became clear. The clear solution was heated for 5 hours, during which time it became cloudy and then opaque and white in color. It was then tested in the same manner as Example 6. The results are shown in Table 2 below. A primary particle diameter could not be calculated due to the amount of scattering present in the UV-visible spectrum.

TABLE 2

| Example Number | $\lambda'_{max}$ (nm) | Primary Particle Diameter (nm) | Agglomerated Particle Diameter (nm) |
|---|---|---|---|
| 6 | 362.3 | 5.4 | 28 |
| C-8 | 369.7 | Not Calculated | 1550 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

I claim:

1. A process comprising
   (a) combining
      (1) at least one base,
      (2) at least one metal carboxylate salt comprising
         (i) a metal cation selected from metal cations that form amphoteric metal oxides or oxyhydroxides and
         (ii) a lactate or thiolactate anion, and
      (3) at least one polar organic solvent; and
   (b) reacting said base and said metal carboxylate salt in the presence of said polar organic solvent to form substantially non-agglomerated metal oxide or metal oxyhydroxide nanoparticles having a diameter of less than 100 nanometers;
   wherein said metal carboxylate salt is selected from carboxylate salts of Ti, V, Mn, Cr, Al, Zn, Ga, In, Sn, Pb, and mixtures thereof.

2. The process of claim 1, wherein said base is a hydroxyl group-containing base.

3. The process of claim 1, wherein said base is selected from the group consisting of sodium hydroxide, potassium hydroxide, ammonium hydroxide, tetramethylammonium hydroxide, and mixtures thereof.

4. The process of claim 1, wherein said metal carboxylate salt is selected from carboxylate salts of Ti, Al, Zn, Ga, In, and mixtures thereof.

5. The process of claim 1, wherein said metal carboxylate salt is a zinc carboxylate salt.

6. The process of claim 1, wherein said anion of said metal carboxylate salt is a lactate anion.

7. The process of claim 1, wherein said metal carboxylate salt is selected from the group consisting of metal carboxylate salts represented by the following general formula $$[CH_3CH(Y)COO^-]_m[X^-]_nM^{+(m+n)} \qquad (I),$$

wherein each Y is independently —OH or —SH; X is a non-interfering anion; m and n are integers having values such that the sum m+n is equal to the charge of the metal cation, M; and at least 90 mole percent of M (based upon the total number of moles of metal cation) is selected from the group consisting of Ti, V, Mn, Cr, Al, Zn, Ga, In, Sn, Pb, and mixtures thereof.

8. The process of claim 7, wherein said Y is —OH; said X is an anion selected from the group consisting of halide, nitrate, acetate, carbonate, formate, propionate, sulfate, bromate, perchlorate, tribromoacetate, trichloroacetate, trifluoroacetate, $R'(OR)_xZ(OR)_w(CH_2)_yCOO^-$
   (wherein R' is a linear or branched alkyl group having from 1 to 4 carbon atoms, each R is independently a linear or branched alkylene moiety having from 1 to 4 carbon atoms, x is an integer of 0 to 4, Z is a divalent organic linking moiety, w is an integer of 0 to 4 with the proviso that the sum of x+w is an integer of 1 to 4, and y is an integer of 0 to 3),
   and chlorate ions, and mixtures thereof; and said M is selected from the group consisting of Ti, Al, Zn, Ga, In, and mixtures thereof.

9. The process of claim 8, wherein said X is selected from the group consisting of chloride, acetate, and mixtures thereof.

10. The process of claim 9, wherein said M is zinc.

11. The process of claim 1, wherein said metal carboxylate salt is selected from the group consisting of metal lactates, metal thiolactates, and mixtures thereof, said metal being selected from the group consisting of Ti, V, Mn, Cr, Al, Zn, Ga, In, Sn, Pb, and mixtures thereof.

12. The process of claim 11, wherein said metal carboxylate salt is selected from the group consisting of metal lactates, metal thiolactates, and mixtures thereof, said metal being selected from the group consisting of Ti, Al, Zn, Ga, In, and mixtures thereof.

13. The process of claim 12, wherein said metal carboxylate salt is selected from the group consisting of zinc lactate, zinc thiolactate, and mixtures thereof.

14. The process of claim 1, wherein said metal carboxylate salt is zinc lactate.

15. The process of claim 1, wherein said metal carboxylate salt is used in combination with at least one other salt, said other salt having only non-interfering anions.

16. The process of claim 15, wherein said other salt is a metal acetate.

17. A process comprising (a) combining (1) at least one hydroxyl-group containing base, (2) at least one metal carboxylate salt selected from the group consisting of zinc lactate, zinc thiolactate, and mixtures thereof, and (3) at least one polar organic solvent; and (b) reacting said base and said salt in the presence of said polar organic solvent to form substantially non-agglomerated zinc oxide or zinc oxyhydroxide nanoparticles having a diameter of less than 100 nanometers.

* * * * *

UNITED STATES PATENT AND TRADEMARK OFFICE
CERTIFICATE OF CORRECTION

PATENT NO. : 8,834,832 B2  Page 1 of 1
APPLICATION NO. : 12/746952
DATED : September 16, 2014
INVENTOR(S) : Timothy Dunbar It is certified that error appears in the above-identified patent and that said Letters Patent is hereby corrected as shown below:

In the Specification

Column 4
Line 14, delete "$Fe^{+3}\ Fe^{+4}$" and insert -- $Fe^{+3}$, $Fe^{+4}$, --, therefor.

Column 5
Line 50, delete "N-methylpyrrolidinone" and insert -- N-methyl pyrrolidinone --, therefor.

Column 6
Line 12, delete "thereof" and insert -- thereof; --, therefor.

Column 7
Lines 40-41, delete "Savitsky-Golay" and insert -- Savitzky-Golay --, therefor.

Column 8
Line 43, delete "Decree" and insert -- Degree --, therefor.

Line 64, delete "Mallincrodt" and insert -- Mallinckrodt --, therefor.

Column 13
Line 5, delete "Mallinkrodt" and insert -- Mallinckrodt --, therefor.

Signed and Sealed this
Twelfth Day of May, 2015

Michelle K. Lee
*Director of the United States Patent and Trademark Office*